US00PP07942P

United States Patent [19]

Moore

[11] Patent Number: Plant 7,942

[45] Date of Patent: Aug. 18, 1992

[54] ROSE PLANT/VAR: MORCHICK

[75] Inventor: Ralph S. Moore, Visalia, Calif.

[73] Assignee: Sequoia Nursery, A Calif. Corp., Visalia, Calif.

[21] Appl. No.: 654,380

[22] Filed: Feb. 1, 1991

[51] Int. Cl.[5] ..... A01H 5/00

[52] U.S. Cl. ..... Plt./9

[58] Field of Search ..... Plt./5, 9

*Primary Examiner*—James R. Feyrer

[57] ABSTRACT

This invention relates to a new and distinct variety of miniature rose plant of dwarf, compact habit, primarily identified by its very double flowers of medium pink color with occasional white stripes.

1 Drawing Sheet

The present invention relates to a new and distinct variety of hardy, dwarf, bush type rose plant of the miniature class; the variety being primarily characterized — as to novelty — by the very double flowers, the petals being generally a light to medium pink with occasional white stripes.

The variety is further characterized by:

An abundance of bloom, with flowers usually borne in sprays or clusters.

Little or slight fragrance.

A plant which is vigorous, of rounded to upright shape with small semi-glossy foliage with pointed leaflets; the buds and flowers being similar in form to Pink Petticoat (miniature — U.S. Plant Pat. No. 4,363).

The plant, which has a normal height of 10–12 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between Climbing Cecile Brunner (Polyantha — not patented) as the seed parent and an un-named seedling (Dortmund × (Fairy Moss × un-named striped Floribunda) as the pollen parent.

Subsequent to origination of the variety I successfully asexually reproduced it at Seqoia Nursery, located as aforesaid, by budding as well as by cuttings; the reproductions having run true in all respects.

The color photograph illustrates the variety including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety identification.*—MORchick.

*Commercial synonym.*—CHICK-A-DEE.

Flowers borne: Usually several together in loose clusters or spray on sturdy, wirey stems.

Quantity of bloom: Abundant both outside and in greenhouse.

Bud:

*Peduncle.*—Medium to short length; slender but sturdy; erect; medium green, sometimes tinted bronze (outdoors); nearly smooth or with some small hair-like apendages.

*Before calyx breaks.*—Size — small. Form — ovoid to pointed, with several small foliaceous apendages on surface of bud; with foliaceous parts extending beyond the tip of the bud equal to less than one-half of its length. Color — medium green, occasionally tinted with bronze (outdoors).

*As calyx breaks.*—Color — pink.

*Opening.*—Opens well in all weather.

Bloom:

*Size when fully open.*—Small, averaging about 30 mm (1¼").

*Petalage.*—Very double, averaging about 60 (or more) petals, arranged regularly plus several small petaloids.

*Form.*—Full, high centered — first becoming rounded with petals rooled loosly outward and downward. Open flowers usually have few or no stamens.

Petals: Fairly thick; satiny on inside and on outside surface.

*Shape.*—Outside petals, broad lanceolate (wedge shaped) with rounded tip; intermediate — broad lanceolate with nearly round or short acute tip; inside — lanceolate with rounded or acute tip.

Color: Newly opened flower from a plant grown outdoors (Nov. 1990), Visalia, Calif.:

*Outside petal.*—Outside surface — medium pink (near Neyron Rose 623/2 or lighter). Inside surface — near Nyron Rose 623/1 to 623/2 (sometimes lighter pink) with some petals occasionally striped with white.

*Intermediate petal.*—Outside surface similar to outside petal. Inside surface — similar to outside petal.

*Inner petal.*—Outside surface similar to intermediate petal: inside surface — similar to intermediate petal.

NOTE: This tendency to sometimes show striped petals is a definite identification of this otherwise pink miniature rose.

*General color effect.*—Newly opened flowers — medium pink. Three days open — color — similar to fresh open flowers, but less bright. Behavior — opens well in all weather. Spent petals or flowers drop off. Flower longevity (Sep. 1990) plant in pot 8-10 days or longer. Cut flowers at living room temperature 5-7 days or longer.

Reproductive organs:

*Stamens.*—Few, usually none.

*Filaments.*—Slender (if present).

*Anthers.*—Few, usually none; yellowish.

*Pollen.*—None.

*Pistils.*—Small number.

*Styles.*—Long — slender; reddish; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; small; leathery; semi-glossy; serrated.

*Leaflets.*—Shape: broad lanceolate; apex acute; base — rounded. Color: medium green; new growth — normal (medium) green (sometimes tinted reddish).

*Rachis.*—Medium strength; upperside usually quite smooth; grooved; underside usually quite smooth, but may have one or two small thorns (or claws) and few or no tiny hairs or prickles.

*Stipules.*—Medium length; medium width; short length narrow points which turn out usually at about 45 degrees or more.

Growth:

*Habit.*—Dwarf; bushy; rounded; much branched.

*Growth.*—Vigorous; internodes; much branched; short.

*Canes.*—Medium; slender; sturdy.

*Main stems.*—Color: medium green.

*Thorns.*—Average number, generally small size and length — slightly hooked or inclined downward. Hairs — usually none.

NOTE: The growth and flowering habit of this variety resembles that of Cinderella (Miniature — U.S. Plant Pat. No. 1,051, expired) but on a slightly larger scale.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers, basically medium pink (with occasional white striped), the bud being pointed in the early opening stage, resembling in form Pink Petticoat (Miniature — U.S. Plant Pat. No. 4,636) with the open flower being very full (double) and rounded with many (60 or more) petals; and further characterized by a plant of compact, vigorous, rounded shape, with main stems and shoots of average thorniness, the said plant being easy to propagate from soft wood cuttings with an abundance of small semi-glossy foliage, the flowers being borne several together in loose clusters or sprays on short to medium length stems.

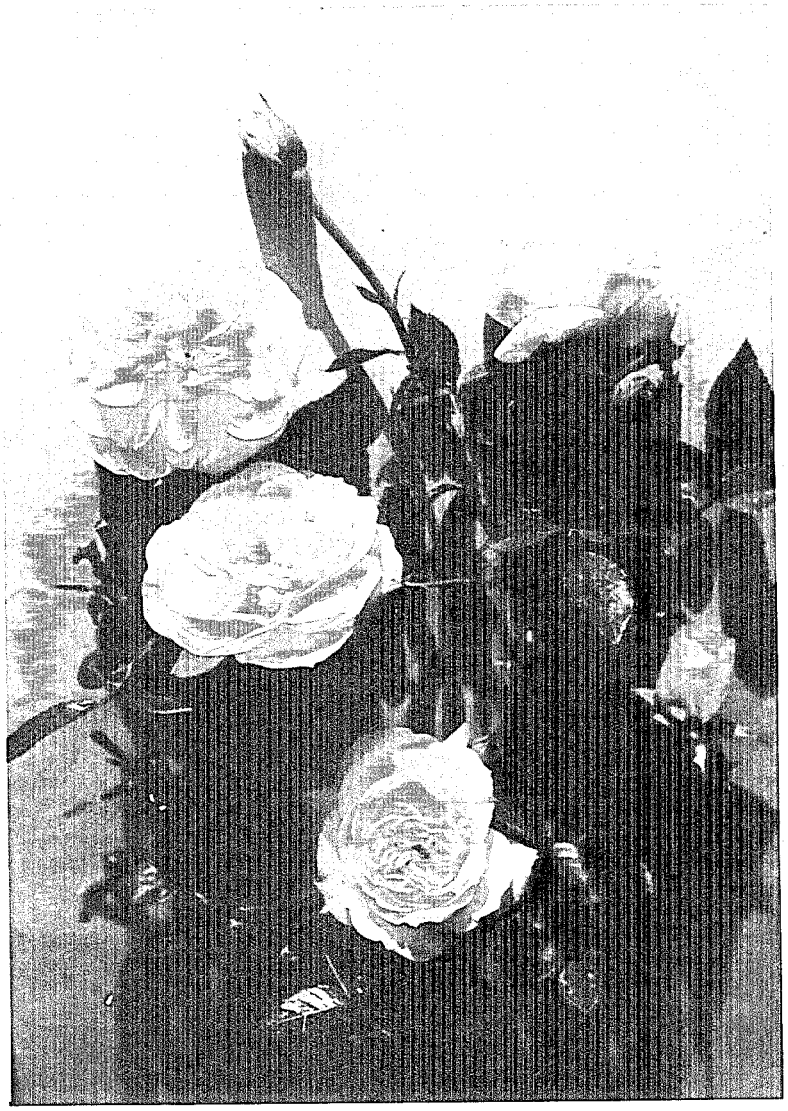

* * * * *